United States Patent [19]
Ander et al.

[11] Patent Number: 5,563,792
[45] Date of Patent: Oct. 8, 1996

[54] VEHICULAR SURFACE TRACTION CHARACTERISTIC ESTIMATION TECHNIQUES

[75] Inventors: Anthony T. Ander, Plymouth; Davorin Hrovat; Craig J. Simonds, both of Dearborn; Lee-Fei Chen, Ann Arbor, all of Mich.

[73] Assignee: Ford Motor Company, Dearborn, Mich.

[21] Appl. No.: 358,842

[22] Filed: Dec. 19, 1994

Related U.S. Application Data

[63] Continuation of Ser. No. 974,636, Nov. 12, 1992, abandoned.

[51] Int. Cl.$^6$ .......................... B60K 28/16; B60K 31/00; B60T 8/56
[52] U.S. Cl. ................. 364/426.02; 364/426.01; 180/197; 361/238
[58] Field of Search ............... 364/424.05, 426.01, 364/426.02, 426.03; 180/197, 140, 142; 361/238

[56] References Cited

U.S. PATENT DOCUMENTS

| | | | |
|---|---|---|---|
| 3,921,446 | 11/1975 | Ludloff | 73/136 |
| 4,680,959 | 7/1987 | Henry et al. | 73/117 |
| 4,758,967 | 7/1988 | Shmuter et al. | 364/550 |
| 4,873,638 | 10/1989 | Shiraishi | 364/426.01 |
| 4,873,639 | 10/1989 | Sato et al. | 364/426.01 |
| 4,882,693 | 11/1989 | Yopp | 364/426.01 |
| 4,947,332 | 8/1990 | Ghonein | 364/426.03 |
| 4,974,694 | 12/1990 | Matsumoto | 180/197 |
| 4,984,163 | 1/1991 | Kuwana et al. | 364/426 |
| 4,985,838 | 1/1991 | Hashiguchi et al. | 364/426 |
| 4,987,966 | 1/1991 | Fujita | 364/426.01 |
| 5,033,573 | 7/1991 | Hrovat | 364/424.05 |
| 5,044,660 | 9/1991 | Yamamura et al. | 364/424.05 |
| 5,123,715 | 6/1992 | Okubo | 364/426.05 |
| 5,132,906 | 7/1992 | Sol et al. | 364/426 |
| 5,159,991 | 11/1992 | Tsuyama et al. | 180/197 |
| 5,163,530 | 11/1992 | Nakamura et al. | 364/426.01 |
| 5,198,982 | 3/1993 | Kobayashi | 364/426 |
| 5,216,608 | 6/1993 | Ito et al. | 364/426.03 |
| 5,229,955 | 7/1993 | Nishiwako et al. | 364/424.05 |
| 5,238,081 | 8/1993 | Maeda et al. | 180/197 |
| 5,243,526 | 9/1993 | Ito et al. | 364/426 |
| 5,265,693 | 11/1993 | Rees et al. | 364/426.01 |
| 5,278,761 | 1/1994 | Ander et al. | 364/426.01 |
| 5,315,519 | 5/1994 | Chin et al. | 364/426.02 |
| 5,351,192 | 9/1994 | Tsuyama et al. | 364/426.01 |
| 5,353,225 | 10/1994 | Tsuyama et al. | 364/426.03 |
| 5,373,447 | 12/1994 | Howes et al. | 364/426.01 |
| 5,379,222 | 1/1995 | Anan et al. | 364/426.03 |
| 5,394,329 | 2/1995 | Bridgens | 364/426.01 |
| 5,408,411 | 4/1995 | Nakamura et al. | 364/426.01 |

OTHER PUBLICATIONS

Igata, et al., 1992, "Development of New Control Methods to Improve Response of Throttle Type Traction Control System", Transmission and Driveline Symposium: Components, Gears, and CAE (SP–905).

*Primary Examiner*—Kevin J. Teska
*Assistant Examiner*—Tyrone V. Walker
*Attorney, Agent, or Firm*—Peter Abolins; Roger L. May

[57] ABSTRACT

A technique for estimating a traction characteristic of a surface under a moving vehicle, such as the coefficient of friction of the surface. The traction characteristic can be estimated by generating a torque signal representative of at least an estimate of the amount of torque applied to the driven wheels of the vehicle. A load signal representative of at least an estimate of the load or weight applied to the driven wheels also is generated. The value of the torque signal is divided by the value of the load signal in order to generate a characteristic signal. Depending on the amount of slippage between the driven and non-driven wheels of the vehicle, the characteristic signal can be stored in order to provide an estimate of the traction characteristic of the surface in real time.

13 Claims, 2 Drawing Sheets

VEHICULAR SURFACE TRACTION CHARACTERISTIC ESTIMATION TECHNIQUES

This is a continuation of application Ser. No. 07/974,636 filed Nov. 12, 1992, now abandoned.

FIELD OF THE INVENTION

This invention is directed to techniques for estimating a traction characteristic of a surface under a moving vehicle, such as the coefficient of friction of the surface. More particularly, the invention is directed to such techniques that are suitable for use in a system for controlling the spin of the driven wheels of a vehicle.

BACKGROUND OF THE INVENTION

Those who drive vehicles on ice, snow or loose gravel frequently have trouble controlling the spin of the vehicle's driven wheels. Such surfaces have a relatively low coefficient of friction which substantially reduces the traction between the driven wheels and the road surface. As a result, even a small amount of torque applied to the driven wheels tends to cause them to spin. If the spin becomes severe, the vehicle can be difficult to control.

As far as the applicants are aware, there is no known technique for accurately estimating the traction characteristics of a surface under a moving vehicle. Such an estimate is difficult, because the surface under a moving vehicle is subject to rapid change. As a result, the traction characteristic must be quickly estimated, and the estimates must be updated at short time intervals in order to assure accurate estimation on a real time basis as the vehicle is being driven.

One paper which refers to a gross estimate of surface adhesion coefficient is entitled "Development of New Control Methods to Improve Response of Throttle Type Traction Control System," by Hiroshi Igata et al., reprinted from Transmission and Driveline Symposium: Components, Gears and CAE (SP-905), bearing the legend "International Congress & Exposition, Detroit, Mich., Feb. 24–28, 1992," available as SAE Technical Paper Series No. 920608. Page 4 of the paper suggests that the adhesion coefficient can be assumed to be at least equal to the acceleration of the vehicle, as measured in terms of G. Page 5 of the paper suggests that the calculated adhesion coefficient should not be revised to a lower value unless wheel slip exceeds a predetermined level.

Experience has shown that a periodically updated estimate of a traction characteristic of a surface in real time provides advantages over an assumption that the adhesion coefficient is equal to the acceleration of the vehicle, as measured in terms of G.

Experience has also shown that an accurate real time estimate of the traction characteristics of the surface under a moving vehicle can be used to help better control wheel spin.

SUMMARY OF THE INVENTION

According to a first aspect of the invention, a method is provided for estimating a traction characteristic of the surface under a moving vehicle that includes a pair of driven wheels and a pair of non-driven wheels. The vehicle is steered from one of the pairs of wheels by a conventional steering wheel. In such a method, the applicants have found it beneficial to generate a plurality of characteristic signals periodically. Each of the characteristic signals is representative of at least an estimate of a traction characteristic of the surface over which the vehicle is moving. First and second speed signals representative of the angular speed of the driven and non-driven wheels, respectively, are generated. The inventors also employ a slip signal responsive at least in part to a difference in value of the first and second speed signals. A wheel angle signal representative of the angle of the steerable pair of wheels with the longitudinal axis of the vehicle is generated. A slip limit signal is generated which depends on the wheel angle signal and which represents a predetermined value of slippage between the driven wheels and the non-driven wheels. Depending on a predetermined relationship between the values of the slip signal and the slip limit signal, a value of one of the characteristic signals is stored so that the traction characteristic of the surface can be estimated in real time. Preferably, the traction characteristic is coefficient of friction.

According to a second aspect of the invention, the traction characteristic of a surface under a moving vehicle is estimated by generating a torque signal representative of at least an estimate of the amount of torque applied to the driven wheels of the vehicle. A load signal is also generated which is representative of at least an estimate of the load or weight applied to the driven wheels. The value of the torque signal is divided by the value of the load signal in order to generate a characteristic signal. The inventors also employ first and second speed signals representative of the angular speed of the driven and non-driven wheels, respectively, of the vehicle. A slip signal is generated which is responsive at least in part to a difference in value of the first and second speed signals. Depending on the value of the slip signal, the characteristic signal can be stored in order to provide an estimate of the traction characteristic of the surface in real time. Preferably, the traction characteristic is coefficient of friction.

Use of the foregoing techniques offer a significant advantage that results in improved estimation of a traction characteristic of a surface under a moving vehicle in real time. By making the slip limit signal dependent on the wheel angle signal, the surface traction characteristic can be estimated with improved accuracy no matter how the driver of the vehicle is moving the steering wheel. In addition, dividing the value of the torque signal by the value of the load signal to generate a characteristic signal is found to be an accurate method of periodically estimating the traction characteristic in real time, especially when coupled with storage of a value of the characteristic signal dependent on the value of the slip signal.

BRIEF DESCRIPTION OF THE DRAWINGS

The detailed description of certain preferred embodiments of the invention is provided below with reference to the accompanying drawings, wherein the same reference numeral is used for a given feature in all figures.

DETAILED DESCRIPTION OF CERTAIN PREFERRED EMBODIMENTS

Figure 1:
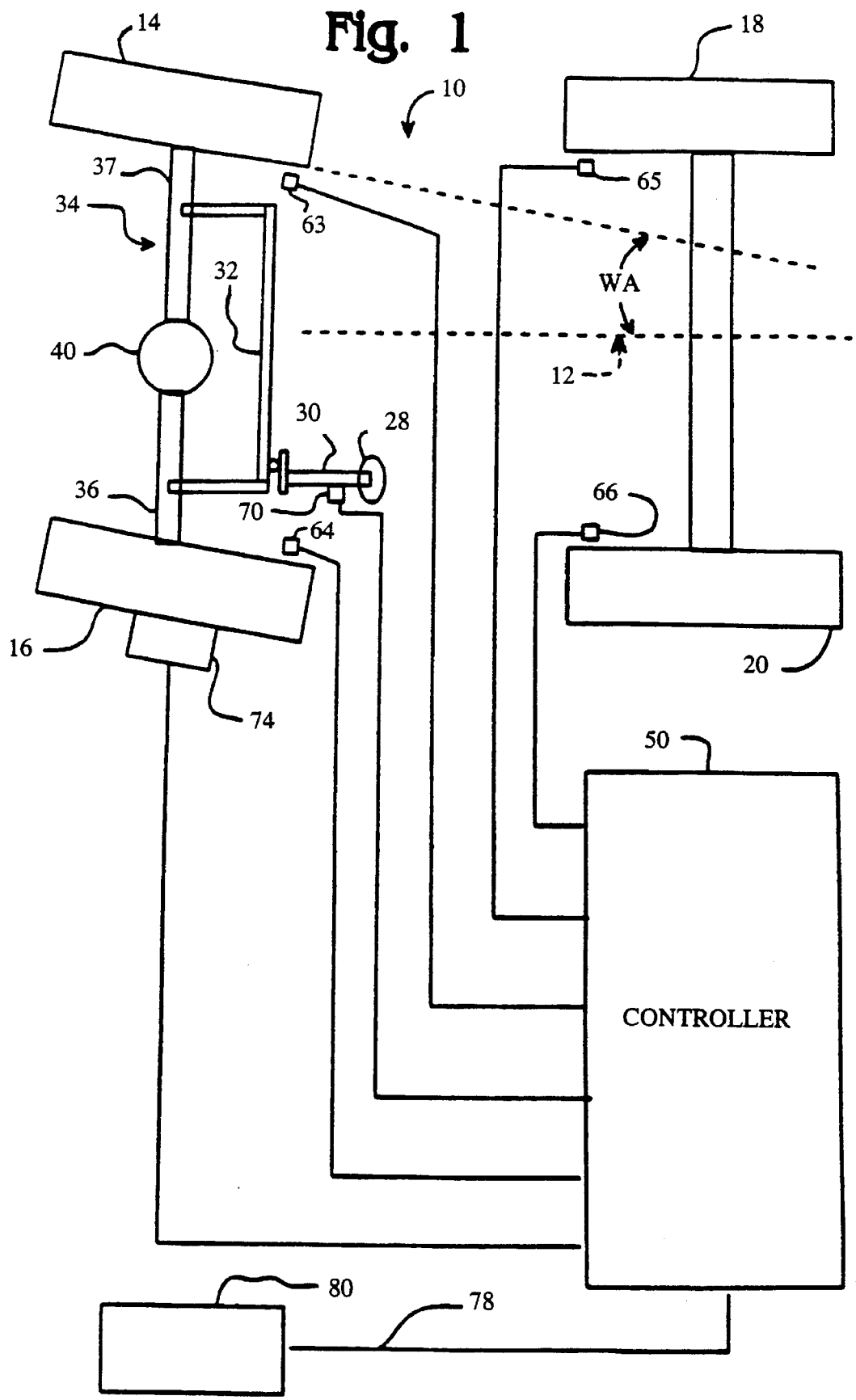
FIG. 1 is a fragmentary, schematic view of an exemplary automobile chassis in which a preferred form of the present invention may be used to advantage.

Referring to FIG. 1, a preferred form of the invention may be used to advantage in an exemplary front wheel drive vehicle 10 defining a longitudinal axis 12. The vehicle includes driven wheels 14 and 16, as well as non-driven wheels 18 and 20. A steering assembly 26 comprises a steering wheel 28 supported by a conventional steering column 30. The steering column is linked to a front axle 34 by conventional steering linkage 32. Front axle 34 includes half axles 36 and 37 that supply power to driven wheels 14 and 16 through a conventional differential 40.

Still referring to FIG. 1, a preferred form of the present invention includes a conventional electronic microprocessor or controller 50 that may be implemented by the electronic engine controller (EEC) manufactured by Ford Motor Company. Inputs to controller 50 are supplied by wheel speed sensors 63–66 for sensing the angular speed of wheels 14, 16, 18 and 20, respectively. A conventional steering angle transducer 70 may be mounted on steering column 30 in order to provide a signal proportional to the steering angle through which steering wheel 28 is moved. One of the driven wheels, such as wheel 16, may be fitted with a commercially available torque sensor 74 for providing a signal proportional to the amount of torque applied to driven wheels 14 and 16. Torque sensor 74 may be a model manufactured by Lucas Schaevitz Company.

Controller 50 has an output port 78 that is connected to a coefficient of friction display 80. Display 80 may be arranged in the form of a bar graph with ten bars representing increments of 0.1 within a range of 0.1 to 1.0 and a set of four lights labeled "Ice,""Snow,""Wet" and "Dry." EEC 50 is programmed to update display 80 approximately every 20 milliseconds. In every update cycle, EEC 50 sends out a reset signal on a reset line and 0 to 10 serial pulses on a data line (not shown). Both the reset line and the data line are connected to display 80. The ice, snow, wet and dry lights are activated through the display unit's own logic and represent coefficient of friction values as follows:

| Surface Condition | Coefficient of Friction Value |
|---|---|
| Ice | 0–0.2 |
| Snow | 0.3–0.5 |
| Wet | 0.6–0.7 |
| Dry | 0.8–1.0 |

Design of display 80 based on the foregoing information is well within the ordinary skill of the electronic art.

Rather than using torque sensor 74, those skilled in the art will recognize that the torque applied to driven wheels 14 and 16 can be estimated by a variety of microprocessor techniques. Exemplary techniques are shown in the following U.S. patents:

| U.S. Pat. No. | Inventor | Issue Date |
|---|---|---|
| 3,921,446 | Ludloff | November 25, 1975 |
| 4,680,959 | Henry et al. | July 21, 1987 |
| 4,758,967 | Shmuter et al. | July 19, 1988 |
| 4,985,838 | Hashiguchi et al. | January 15, 1991 |

A preferred form of torque estimation is described and claimed in co-pending application entitled "Robust Torque Estimation Using Multitudes Of Models" assigned to the Ford Motor Company and filed in the names of Davorin Hrovat and Lee-Fei Chen on the same date as the present application. EEC 50 is programmed to perform the method steps described in connection with FIG. 2. In step 100, the value of a torque signal representative of at least an estimate of the amount of the torque applied to driven wheels 14 and 16 is stored in the memory of EEC 50 at memory location Torque_Estimated. The torque signal can be generated either by torque sensor 74 or a program for estimating torque of the type previously described. A steering angle signal representative of the steering angle of steering wheel 28 is generated by steering angle transducer 70 and is stored in the memory of EEC 50 at memory location Steering_Angle. Speed signals representative of the angular speed of the wheels are received from sensors 63–66 and are stored in the memory of EEC 50. At a memory location Load, EEC 50 stores a value of a load signal representative of an estimate of the normal force applied to driven wheels 4 and 16 by the dynamic weight of vehicle 10 during normal operation.

EEC 50 generates a first speed signal representative of the angular speed of the driven wheels by averaging the speed signals received from sensors 63 and 64. EEC 50 generates a second speed signal representative of the angular speed of the non-driven wheels by averaging the value of the speed signals received from sensors 65 and 66, respectively.

In step 110, a current estimate of the coefficient of friction of the surface under vehicle 10 is estimated by having EEC 50 divide the value of the torque signal by the value of the load signal. The torque signal and load signal are generated from the corresponding values stored in memory. The value of the signal resulting from the division is stored in a memory location $Mu_{temp}$ as a current but temporary estimate of the coefficient of friction of the surface under the vehicle. The calculation of the $Mu_{temp}$ value is an important feature which provides an accurate estimate of the current coefficient of friction of the surface under the vehicle after processing by the other operating parts of the program described in steps 120–170.

In step 120, an initial coefficient of friction value, $Mu_o$ is calculated by setting the value to approximately 0.8–0.9. The range of the coefficient of friction according to the preferred embodiment is 0.0–1.0.

In step 120, a slip limit signal $S_L$ representative of a predetermined value of slippage between the driven wheels and the non-driven wheels is calculated. Signal $S_L$ is equal to a constant plus the value of the steering angle signal from transducer 70 multiplied times a factor which represents increased slip requirements in turns, taking into account conversion of the steering angle signal into a wheel angle signal representative of the angle between the steerable pair of wheels 14 and 16 and longitudinal axis 12. In FIG. 1, the steering wheel angle is shown by the angle Wa.

Figure 2:
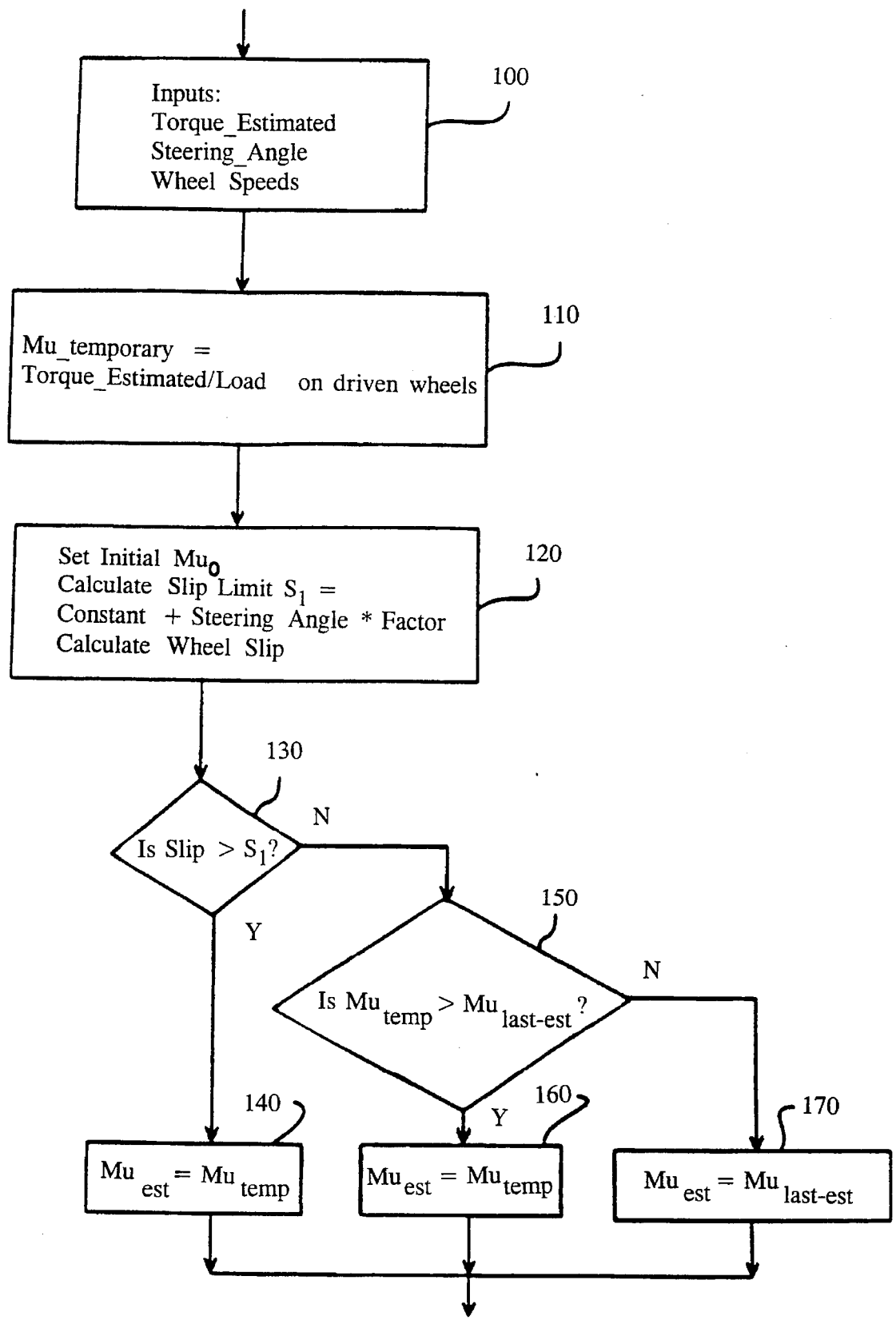
FIG. 2 is a flow diagram illustrating the operation of an exemplary controller operating in accordance with a preferred embodiment of the present invention in order to estimate the coefficient of friction of a surface under a moving vehicle in real time.

In step 120 of FIG. 2, a wheel slip signal (Slip) is generated by calculating the absolute value of the difference between the first speed signal and the second speed signal. Thus, the slip signal is a measure of the amount of slippage between the driven wheels and the non-driven wheels. Use of the steering angle in step 120 is an important feature that increases the accuracy of the slip limit value. The slip limit value should change when the driver of the vehicle turns the steering wheel. The tractive force generated by driven wheels 14 and 16 is reduced, for the same slip value, when steering around a corner. During cornering, the force of the wheels against the surface is divided into a tractive force component and a cornering force component. The proper value of the slip limit signal increases with aggressive gas pedal positioning during cornering and is calculated in step 120.

In step 130, EEC 50 generates a first decision signal if the slip signal is greater than the value of the slip limit signal. If the value of the slip signal is not greater than the value of the slip limit signal, as shown in step 130, EEC 50 generates a second decision signal.

In response to the first decision signal, in step 140, the temporary value of the coefficient of friction stored at location $Mu_{temp}$ is transferred to memory location $Mu_{est}$ which, after each processing cycle, represents the estimated coefficient of friction of the surface under vehicle 10. This is an important feature that substantially improves the accuracy of the coefficient of friction estimate. Experience has shown that the coefficient of friction estimate made in step 110 is only accurate if the slip signal has a predetermined range of values with respect to the slip limit signal. If the slip signal has a value greater than the slip limit signal, then the temporary coefficient of friction estimate is sufficiently accurate to replace the previously stored estimate ($Mu_{Last-est}$).

As shown in step 150, in response to the second decision signal, if the temporary coefficient of friction estimate stored at location $Mu_{temp}$ is greater than the previously stored coefficient of friction estimate ($Mu_{Last-est}$), a third decision signal is generated by EEC 50. If the temporary coefficient of friction estimate is not greater than the previously stored estimate ($Mu_{Last-est}$), EEC 50 generates a fourth decision signal.

As shown in step 160, in response to the second and third decision signals, the value of memory location $Mu_{est}$ is set equal to the temporary coefficient of friction estimate calculated in step 110. This is an important feature which enables the improved accuracy of the estimate. Experience has shown that if the temporary coefficient of friction estimate is increasing, it is likely that the actual value of the coefficient of friction is increasing, even though there is insufficient wheel slippage between the driven and non-driven wheels to make the value of the slip signal greater than the value of the slip limit signal. These conditions are likely to be encountered when the vehicle is traveling from a lower coefficient of friction surface to higher coefficient of friction surface. Therefore, it is reasonable to assume that the actual value of the coefficient of friction is increasing. As a result, the temporary value of the coefficient of friction, which is greater than the last stored value, is used in step 160 for the new estimate of the actual coefficient of friction.

As shown in step 170, in response to the second and fourth decision signals, memory location $Mu_{est}$ continues to store the previous coefficient of friction estimate ($Mu_{Last-est}$), rather than the temporary estimate calculated in step 110. This is an important feature which increases the accuracy of the estimate. Experience has shown that when the slippage of the driven wheels with respect to the non-driven wheels falls below the criteria stated in step 130 and the temporary coefficient of friction estimate is not greater than the previous estimate, the previous estimate is the best estimate of the actual value of the coefficient of friction of the surface under the vehicle. Accordingly, as shown in step 170, location $Mu_{est}$ continues to store the previously stored estimate ($Mu_{Last-est}$).

EEC 50 is programmed to rapidly execute all of the steps shown in FIG. 2 and then return to repeat the steps again periodically. According to the preferred embodiment, the cycle of steps shown in FIG. 2 is repeated approximately every 20 milliseconds. This is an important feature which enables sufficiently rapid calculation in order to provide an accurate estimate of the coefficient of friction of a surface under vehicle 10 in real time.

The various preferred versions or embodiments of the invention described in detail above are intended only to be illustrative of the invention. Those skilled in the art will recognize that modifications, additions and substitutes can be made in the various features and elements of the invention without departing from the true scope and spirit of the invention. The following claims are intended to cover the true scope and spirit of the invention.

We claim:
1. A method of controlling spin of driven wheels of a moving vehicle with the aid of computer processing means, said moving vehicle traveling over a surface and including a pair of driven wheels and a pair of non-driven wheels, said method comprising the steps of:
   generating a plurality of characteristic signals periodically, each of said characteristic signals being representative of at least an estimate of a traction characteristic of a surface under said moving vehicle;
   generating a first speed signal representative of the angular speed of said driven wheels;
   generating a second speed signal representative of the angular speed of said nondriven wheels;
   generating a slip signal responsive at least in part to a difference in value of said first speed signal and said second speed signal;
   generating a slip limit signal representative of a predetermined value of slippage between said driven wheels and said non-driven wheels;
   generating a first decision signal if the value of said slip signal is greater than the value of said slip limit signal;
   generating a second decision signal if the value of a current one of said characteristic signals is greater than a value of a previously stored one of said characteristic signals;
   storing a value of a current one of said characteristic signals in place of a previously stored value of one of said characteristic signals in response to said first decision signal or in response to said second decision signal to provide a real-time estimate of a traction characteristic of said surface; and
   controlling said driven wheels using said estimate of a traction characteristic of said surface.

2. A method, as claimed in claim 1, wherein said slip signal is proportional to the difference between the angular speed of said driven wheels and the angular speed of said nondriven wheels.

3. A method, as claimed in claim 1, wherein said traction characteristic is coefficient of friction and wherein said characteristic signals are representative of at least an estimate of the coefficient of friction of said surface.

4. A method, as claimed in claim 1 and further comprising the step of displaying the value of said characteristic signal.

5. A method of controlling spin of driven wheels of a moving vehicle with the aid of computer processing means, said moving vehicle traveling over a surface and defining a longitudinal axis and including a pair of driven wheels and a pair of non-driven wheels, one of said pairs of said driven wheels and said non-driven wheels being steerable by a steering wheel, said method comprising the steps of:
   generating a torque signal representative of at least an estimate of the amount of torque applied to said driven wheels;
   generating a load signal representative of at least an estimate of the weight applied to said driven wheels;
   dividing the value of said torque signal by the value of said load signal in order to generate a characteristic signal representative of a traction characteristic of said surface under said moving vehicle;
   generating a first speed signal representative of the angular speed of said driven wheels;
   generating a second speed signal representative of the angular speed of said non-driven wheels;
   generating a slip signal responsive at least in part to a difference in value of said first speed signal and said second speed signal;

generating a first decision signal if the value of said slip signal is greater than a predetermined value;

generating a second decision signal if a current value of said characteristic signal is greater than a previously stored value of said characteristic signal;

storing a current value of said characteristic signal in place of a previously stored value of one of said characteristic signals in response to said first decision signal in response to said second decision signal to provide a real-time estimate of a traction characteristic of said surface; and controlling said driven wheels using said estimate of a traction characteristic of said surface.

6. A method, as claimed in claim 5, wherein said traction characteristic is coefficient of friction.

7. A method, as claimed in claim 5, and further comprising the step of displaying the value of said characteristic signal.

8. A method, as claimed in claim 5, wherein said slip signal is proportional to the difference between the angular speed of said driven wheels and the angular speed of said nondriven wheels.

9. A method, as claimed in claim 8, wherein said predetermined value is obtained by the steps of generating a wheel angle signal representative of the angle between said steerable pair of wheels and said longitudinal axis;

generating a slip limit signal representative of a predetermined value of slippage between said driven wheels and said nondriven wheels dependent on said wheel angle signal; and using the value of said slip limit signal as said predetermined value, and wherein said step of generating said wheel angle signal comprises the steps of:

generating a steering angle signal representative of the steering angle of said steering wheel; and multiplying the value of said steering angle signal by a conversion factor representing different slip requirements while in turns including conversion of said steering angle signal into said wheel angle signal.

10. A method, as claimed in claim 8, wherein said step of generating said slip limit signal comprises the step of adding said scaled wheel angle signal to a constant.

11. A method of controlling spin of driven wheels of a moving vehicle with the aid of computer processing means, said moving vehicle defining a longitudinal axis and including a pair of driven wheels and a pair of non-driven wheels, said method comprising the steps of:

generating a plurality of characteristic signals periodically, each of said characteristic signals being representative of at least an estimate of said traction characteristic, the step of generating a characteristic signal comprising the sub-steps of generating a torque signal representative of at least an estimate of the amount of torque applied to said driven wheels, generating a load signal representative of at least an estimate of the normal force applied to said driven wheels, and dividing the value of said torque signal by the value of said load signal in order to generate one of said plurality of characteristic signals;

generating a first speed signal representative of the angular speed of said driven wheels;

generating a second speed signal representative of the angular speed of said nondriven wheels;

generating a slip signal responsive at least in part to a difference in value of said first speed signal and said second speed signal;

generating a slip limit signal representative of a predetermined value of slippage between said driven wheels and said non-driven wheels;

generating a first decision signal if the value of said slip signal is greater than the value of said slip limit signal;

generating a second decision signal if the value of a current one of said characteristic signals is greater than a value of a previously stored one of said characteristic signals;

storing a value of a current one of said characteristic signals in place of a previously stored value of one of said characteristic signals in response to said first decision signal or in response to said second decision signal to provide a real-time estimate of a traction characteristic of said surface; and controlling said driven wheels using said estimate of a traction characteristic of said surface.

12. A method, as claimed in claim 11, further comprising the step of generating a wheel angle signal representative of the angle between said steerable pair of wheels and said longitudinal axis, and wherein said step of generating said slip limit signal comprises the step of adding a scaled value of said wheel angle signal to a constant.

13. A method, as claimed in claim 12, wherein said step of generating said wheel angle signal comprises the steps of:

generating a steering angle signal representative of the steering angle of said steering wheel; and multiplying the value of said steering angle signal by a conversion factor to convert said steering angle signal into said wheel angle signal.

\* \* \* \* \*